United States Patent [19]

Singer et al.

[11] Patent Number: 5,133,341
[45] Date of Patent: Jul. 28, 1992

[54] KNEE BRACE WITH POSTERIOR STRUT

[76] Inventors: Samuel Singer, 125 Timbersprings La.; Jeffrey A. Fried, 499 S. Ben Franklin Rd., both of Indiana, Pa. 15701

[21] Appl. No.: 662,879

[22] Filed: Mar. 1, 1991

[51] Int. Cl.$^5$ .............................................. A61F 5/00
[52] U.S. Cl. ........................................ 602/16; 602/26
[58] Field of Search ................. 128/80 C, 80 R, 80 F, 128/87 R, 88

[56] References Cited

U.S. PATENT DOCUMENTS

| | | |
|---|---|---|
| 1,092,836 | 4/1914 | Hart . |
| 2,144,641 | 1/1939 | Snyder . |
| 2,179,903 | 11/1939 | Spears . |
| 2,625,453 | 1/1953 | Lampe et al. ................ 128/80 C |
| 3,026,869 | 3/1962 | Peach ........................... 128/80 F |
| 3,194,233 | 4/1965 | Peckham . |
| 3,581,741 | 6/1971 | Rosman et al. . |
| 3,669,105 | 6/1972 | Castiglia . |
| 3,712,299 | 1/1973 | Voehl ............................. 128/80 C |
| 4,088,130 | 5/1978 | Applegate . |
| 4,353,361 | 10/1982 | Foster . |
| 4,372,298 | 2/1983 | Lerman . |
| 4,493,316 | 1/1985 | Reed et al. . |
| 4,572,170 | 2/1986 | Cronk et al. ................... 128/80 C |
| 4,796,610 | 1/1989 | Cromartie ...................... 128/80 C |

FOREIGN PATENT DOCUMENTS

| | | | |
|---|---|---|---|
| 2552660 | 4/1985 | France ........................... | 128/80 C |
| 2581859 | 11/1986 | France ........................... | 128/80 C |
| 2215213 | 9/1989 | United Kingdom ............ | 128/80 C |

*Primary Examiner*—Robert Bahr
*Assistant Examiner*—Linda C. M. Dvorak
*Attorney, Agent, or Firm*—Richard V. Westerhoff

[57] ABSTRACT

A knee brace has a rigid posterior strut behind the knee joint in the popliteal area with terminal portions adjacent, but spaced from the lateral and medial sides of the knee. A prophylactic embodiment of the invention has a lateral inferior rigid support member pivoted on the lateral terminal portion of the strut and secured to the leg, and a medial superior rigid support member pivoted on the medial terminal portion of the strut and secured to the thigh. Stiff anterior, generally triangular, cuff members each have one edge secured to one of the rigid support members and an opposite vertex detachably, pivotally secured to the opposite terminal portion of the strut. A functional brace in accordance with the invention has both lateral and medial rigid support members pivoted on the terminal portions on the posterior strut, additional stiff anterior generally triangular cuffs crisscrossing above and below the knee join and stiff posterior cuffs between the pairs of rigid support members. The posterior strut diverts forces applied to either the leg or thigh around and away from the knee joint and into the large muscles in the other limb member. The position of the strut is automatically adjusted by the soft tissue of the thigh and leg during flexion to center the brace and allow for femoral rollback. Flexion and extension can be selectively limited and additional stabilizing devices may be attached to the terminal portions of the rigid posterior strut.

14 Claims, 4 Drawing Sheets

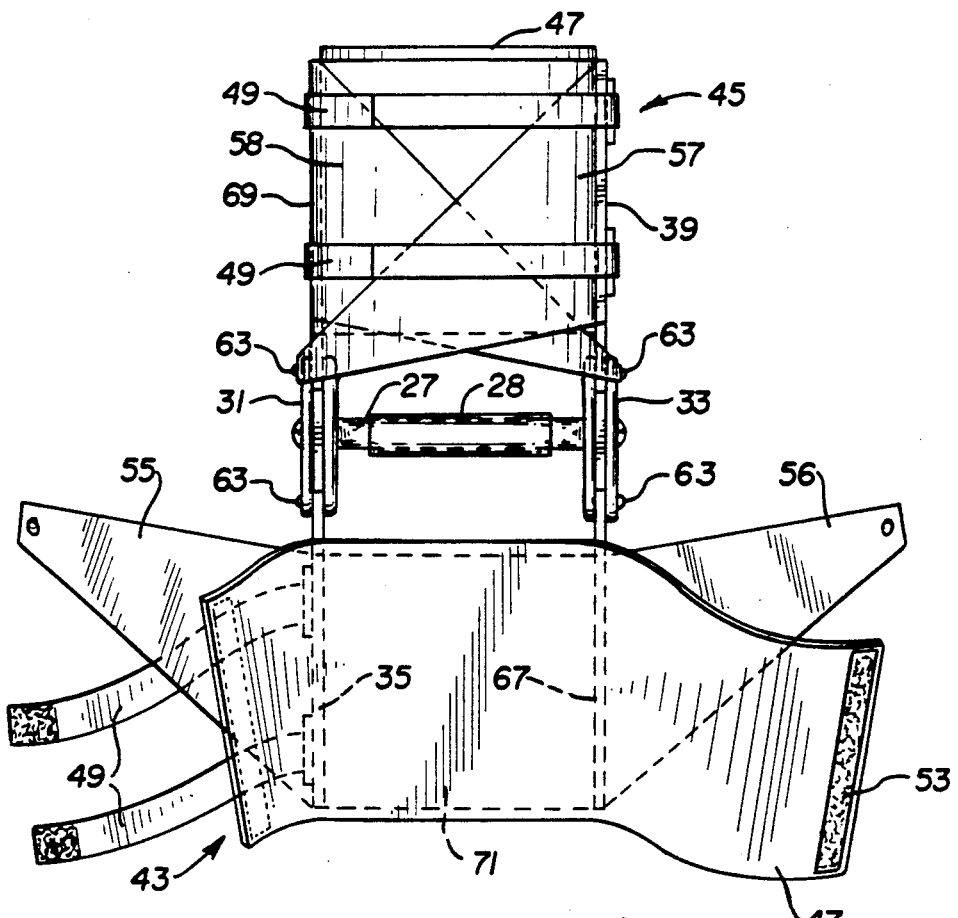
FIG_3
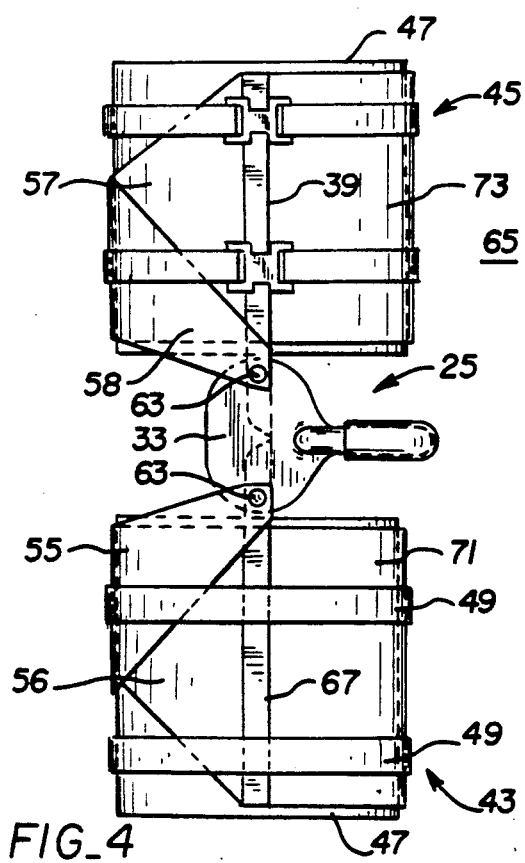
FIG_4

KNEE BRACE WITH POSTERIOR STRUT

BACKGROUND OF THE INVENTION

1. Field of the Invention

This invention relates to an orthopedic support device, specifically a rear strut stabilized, derotational knee brace which may be used for prophylactic, functional and rehabilitative applications.

2. Background Information

Generally knee braces may be classified according to the function they perform. Prophylactic knee braces are used to reduce the likelihood of injury during activities, particularly sports, in which high loads are placed on the knee joint. Usually, an objective of prophylactic knee braces is to provide some support for the joint without unduly restricting movement, thus reducing the risk of injury to a normal knee joint. Functional knee braces are used to support and stabilize injured joints, and hence, provide the strongest reinforcement for the knee. They often prohibit certain movements. Rehabilitative knee braces are used to support previously injured joints and are used extensively during post operative and rehabilitation periods. Their designs generally lie between prophylactic and functional braces in the amount of support they provide, and the degree of restriction they impose on joint movement is usually adjustable to provide only a specific range of desired motion.

Prophylactic supports for the knee joint include wraps of adhesive or elastic tape and reinforced neoprene sleeves. These devices, however, do not provide the support generally required. Prophylactic knee braces have been designed as single hinged vertical members placed laterally on one side of the leg and held by cuffs and straps to the thigh and the leg. Since the anatomy in the knee region is naturally offset, the fixation on one side cannot support the brace effectively. These braces tend to slip, thus exerting undue forces acting against the natural kinematics on the knee joint, and also concentrate forces laterally on the knee, which in some cases, increases the risk of medial collateral ligament or anterior cruciate ligament injury. Several studies have demonstrated the ineffectiveness of such braces in preventing knee injury and in some cases, have demonstrated an increase in foot and ankle injuries as well. This may be due to the slippage of the brace which may cause interference with normal kinematic operation of the knee. This results in fatigue of the thigh and leg muscles, increasing the strain on knee ligaments and the knee joint, thus increasing the risk of injury. In addition, the medial collateral ligament can be preloaded by a lateral brace, increasing the probability of a medial collateral ligament rupture. The bunching up of the support materials in the popliteal space behind the knee, in braces which utilize "fillers" between parts, further contributes to this problem.

Functional knee braces typically have medial and lateral rigid supports for the knee joint. Many of these devices have complicated hinge structures designed to accommodate for the femoral rollback which occurs upon flexion of the knee joint. Some of these braces use rigid molded thigh and leg cuffs to support the hinged lateral and medial support members. Other braces have utilized spiral structures and straps to connect the thigh and leg cuffs. These devices have not proven as effective as desired to protect against a knee injury and to support and stabilize an unstable knee or protect an injured knee. The major disadvantage of these rigid braces is slippage due to the conical shape of the lower extremity. With slippage, even a well designed brace can alter the kinematics of the knee and increase the risk of injury. Altering the normal motion of the knee also causes muscle fatigue, thus, increasing risk of injury. These braces with rigid molded cuffs which capture the knee, prevent the musculature surrounding the knee from effectively absorbing the forces induced around the joint. Existing functional braces have not been proven to effectively control anterior instability at high loads.

Another type of knee brace uses an adjustable rigid or semi-rigid member encircling the knee joint which clamps lateral and medial pads against the knee joint. The proper operation of such braces depends on the exact fit on a specific knee, and therefore must be custom fitted. They are also bulky and generally more expensive. These devices tend to unduly restrict motion of the knee joint. Because of their more complex nature and bulkiness, interference with normal knee operation is higher if the hinge is misaligned.

There remains a need therefore for an improved knee brace for prophylactic, functional and rehabilitative applications.

There is also a need for such an improved knee brace which provides the required support for the knee without undue restriction on the natural movement of the joint.

There is also a need for such an improved knee brace which does not increase the risk of injury.

There is a further need for such an improved knee brace which distributes the load to the fleshy parts of the thigh and leg.

There is yet another need for such an improved knee brace which reduces both shear and torsion forces applied to the knee.

There is still another need for such an improved knee brace which does not slip out of position or bind.

There is an additional need for such an improved knee brace which is light weight and easy to apply and remove.

SUMMARY OF THE INVENTION

These and other needs are satisfied by the invention which is directed to a knee brace which includes a rigid posterior strut located in the popliteal space of the knee and to which all other parts of the brace are attached. The popliteal space behind the knee is the ideal location for fixing the reference point for a knee brace because (a) a rigid strut in the popliteal space does not interfere with the natural motion of the knee and/or the natural action of the leg; (b) any external forces acting on the knee through the mechanical strut are least likely to cause injury to the wearer, since the popliteal space is the only part of the knee where there is adequate soft tissue to absorb harmful energy; (c) the flexion and extension action of the knee relocates the brace into its proper position due to the action of the soft tissue in the popliteal region on the strut; and (d) the posterior strut provides a fixed reference point to which other functional parts of the brace may be attached giving design flexibility for prophylactic, functional and rehabilitative applications.

Because the knee brace of this invention has a posterior strut to which vertical supports are connected by hinges, laterally applied forces at the knee are transmitted to the medial side of the brace, thus preventing injury to the medial collateral ligament. Also, medially directed forces are transmitted to the lateral side, by-passing the knee joint.

The embodiment of the knee brace of this invention for prophylactic applications has a lateral inferior rigid support member which attaches to the leg, and a medial superior rigid support member which attaches to the lower thigh. Both of the rigid support members are pivotally connected on terminal portions of the rigid posterior strut. The pivot points are selected to reproduce the natural kinematics of the knee joint, including posterior femoral rollback. In the preferred form of the brace, stiff cuff members, preferably generally triangular in shape, are secured to the rigid support members and extend around the front of the thigh and calf and are pivotally connected to the opposite terminal portion of the posterior strut. The rigid support members are secured to the leg and thigh, respectively, by anchor means, preferably in the form of soft, resilient sleeves which may be held in place by straps secured such as by VELCRO fasteners. Any open spaces between the rigid support members, cuffs, thigh and calf are filled by the resilient sleeves, which, however, do not extend around the knee joint.

The rigid posterior strut transfers forces acting on the knee around critical areas, dissipating some of the forces so transferred into the soft tissue surrounding the popliteal space. The action of the soft tissues on the posterior strut during normal extension/flexion of the knee causes the brace to self-center. The rigid posterior strut also serves as a known fixed anchor point for the elongated hinged members and the upper and lower cuffs, and may be used to attach any reinforcing, adjusting or motion correcting straps which may be desired for a specific injury. The upper and lower stiff cuffs attached as they are over the soft, resilient sleeves distribute forces acting on the knee through a wide area of the primarily soft tissue in the medial thigh and lateral upper leg areas. They also assist the rigid posterior strut in transmitting torsional forces around the knee joint.

For functional and rehabilitative applications, the brace includes a superior lateral elongated member secured to the thigh and pivotally connected to the lateral terminal portion of the rigid posterior strut and a medial elongated member secured to the leg and pivotally connected to the medial terminal portion of the rigid posterior strut. Thus, in this embodiment of the invention, elongated members extend medially and laterally along both the thigh and the leg to provide additional stability and support for the knee joint. Preferably, posterior stiff cuff members extend between the rigid support members behind the leg and the thigh to firmly capture the lower thigh and upper leg above and below the knee joint. This leaves the knee joint free, and, unlike other braces which capture the knee, this device maintains proper alignment of the pivot points of the elongated members through positioning of the rigid posterior strut during flexion by the soft tissue of the popliteal area. Preferably, additional anterior, generally triangular, stiff cuff members extend from the superior lateral rigid support member and the inferior medial rigid support member to the opposite terminal portion of the rigid posterior strut.

BRIEF DESCRIPTION OF THE DRAWINGS

A full understanding of the invention can be gained from the following description of the preferred embodiments when read in conjunction with the accompanying drawings in which:

FIG. 3 is a front elevation view of a knee brace in accordance with another embodiment of the invention.

FIG. 4 is a side elevation view of the knee brace of FIG. 3.

DESCRIPTION OF THE PREFERRED EMBODIMENTS

Figure 1:
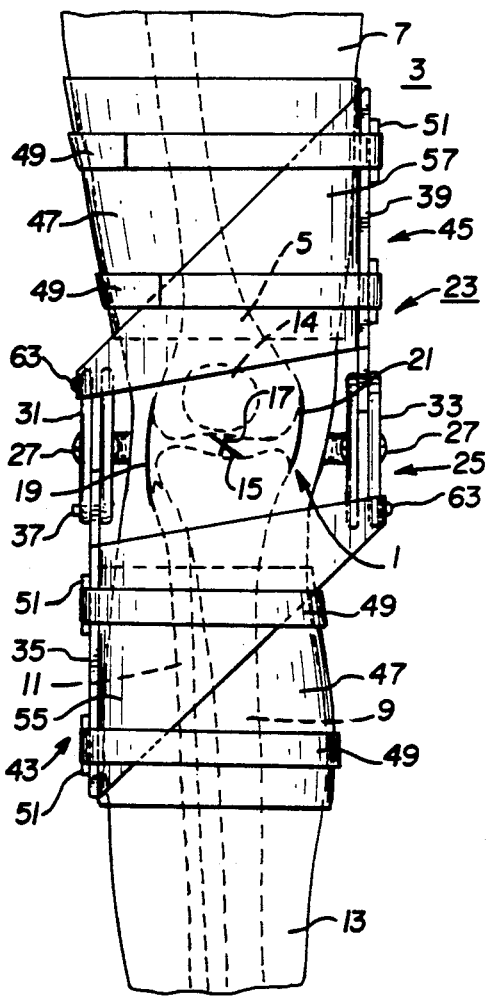
FIG. 1 is a front elevation view of a knee brace in accordance with one embodiment of the invention shown in use.

FIG. 1 illustrates a knee brace in accordance with the invention in use in supporting and stabilizing a knee joint 1 of a human right lower extremity 3. The knee joint 1 is formed by the enlarged ends of the femur 5, which is the bone of the thigh 7, and the upper end of the tibia 9 which together with the fibula 11 form the bones of the leg 13. The patella (knee cap) 14 articulates with the distal end of the femur 5.

The joint 1 is held together by an arrangement of ligaments including the anterior cruciate ligament 15, the posterior cruciate ligament 17, the lateral collateral ligament 19 and the medial collateral ligament 21. Shear forces and torsional forces applied to the knee joint can result in stretching, and even tearing of these ligaments. A common injury occurs when a lateral blow is applied to the outside of the thigh with the foot planted. This causes the knee joint to buckle inward resulting in tearing of the medial collateral ligament 21, and occasionally the anterior cruciate ligament as well.

Figure 2:
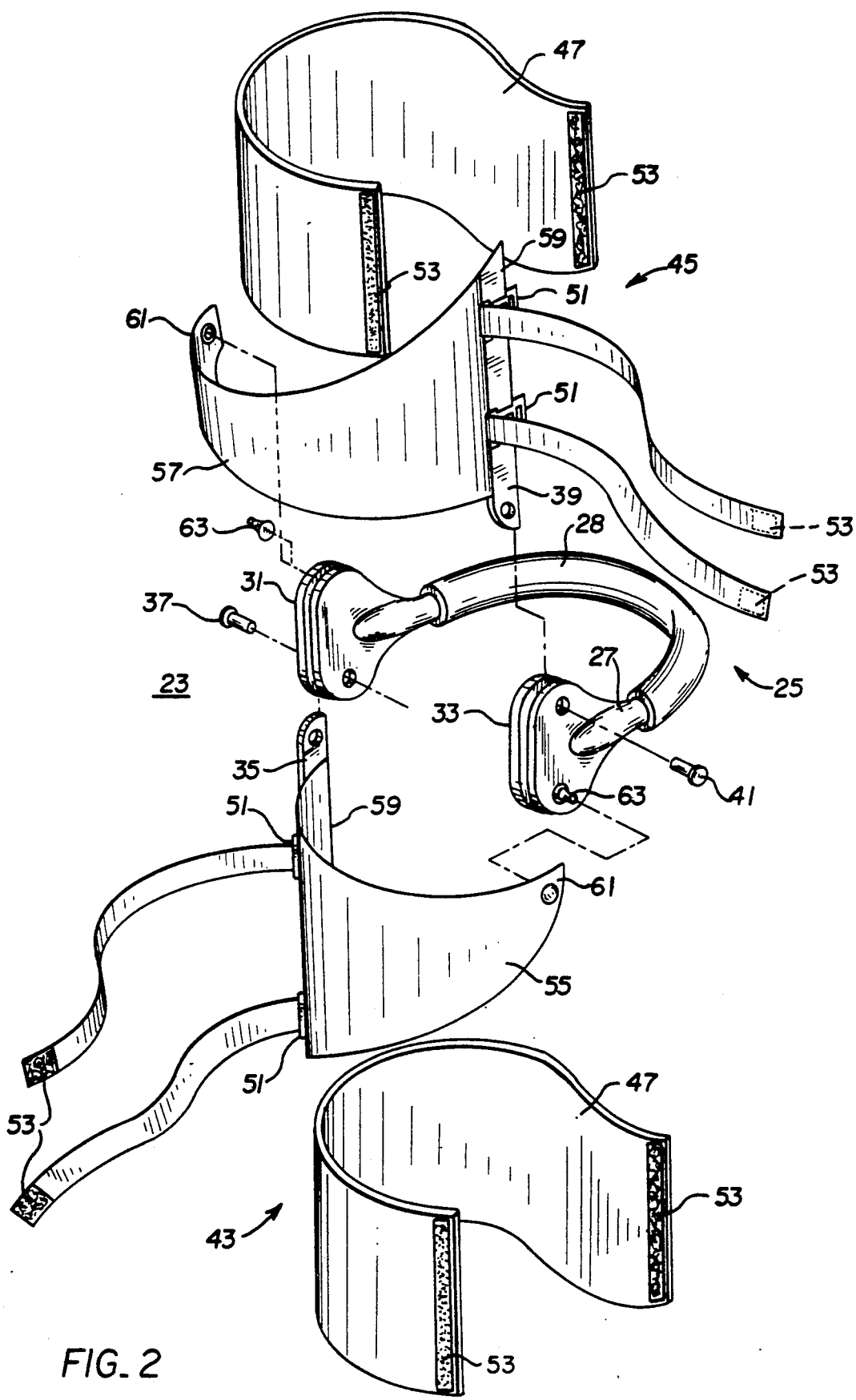
FIG. 2 is an exploded isometric view of the knee brace of FIG. 1.

The knee brace 23 shown in FIGS. 1 and 2 is a prophylactic brace. It includes a rigid posterior strut 25. The strut 25 has an arcuate section 27 which extends behind the knee joint 1 through the popliteal area 29 (see FIG. 5) and terminates in enlarged terminal portions 31 and 33 adjacent, but spaced from the lateral and medial sides, respectively, of the joint 1. If desired, the arcuate section 27 can be covered by a soft resilient sleeve 28.

An inferior lateral rigid elongated support member 35 is pivotally connected to the lateral terminal portion 31 of the rigid posterior strut 25 at a first pivot point by a pivot pin 37 and extends down along the lateral side of the leg 13. A superior medial rigid elongated support member 39 is pivotally connected to the terminal portion 33 of the rigid posterior strut 25 at a second pivot point by pivot pin 41, and extends upward medially along the thigh 7.

The support members 35 and 39 are secured to the leg 13 and thigh 7 respectively by anchoring devices 43 and 45. The anchoring devices 43 and 45 each include a sleeve 47 of a non-slip, cushioning material, such as for instance, neoprene, and a pair of straps 49 which are threaded through buckles 51 on the support member 35 and 39 and secured by VELCRO fasteners 53. These anchoring devices 43 and 45 firmly secure the support members 35 and 39 to fleshy portions of the leg 13 and thigh 7, respectively, so that forces are transmitted through these support members into the large muscles of the extremity 3.

The prophylactic brace 23 is also provided with a pair of stiff, semirigid anterior cuff members 55 and 57. These cuff members are generally triangular in shape with one edge 59 secured to the associated elongated support member 35 or 39, and with the opposing vertex 61 pivotally connected such as with a snap fastener 63 to a connection point on the terminal portion 31 or 33 of the rigid posterior strut 25 opposite to the terminal portion to which the associated support member 35 or 39 is secured. The pivots formed by the fasteners 63 are laterally aligned with the corresponding pivot points of the elongated members to which the cuffs are attached along the edge 59. The cuff members 55 and 57 are unsnapped and opened for applying the brace 23 to the extremity 3, and then are wrapped around in front of the thigh and leg and snapped in place.

With the prophylactic brace 23 in place, lateral blows to the leg 13 are partially absorbed by the muscles in the leg 13 with the remainder transmitted through the posterior rigid strut 25 to the elongated medial support member 39 which pulls the thigh 7 laterally with the leg and dissipates the transmitted energy into the muscles of the thigh. For a lateral blow to the thigh 7, the force not absorbed by the thigh muscles is transmitted by the elongated support 39, around the knee joint 1 by the rigid posterior strut 25, and through the elongated support member 35 into the fleshy portion of the leg 13. The torsion force generated by rotation of the thigh 7 with the foot planted is transmitted around the knee joint 1 by the rigid posterior strut 25, and through the elongated member 35 into the leg 13. The stiff cuff members 55 and 57 help to balance the rotational forces and to dissipate additional energy into the leg muscles. Anterior and posterior forces applied to the leg 13 or the thigh 7 are similarly transmitted around the knee joint 1 through the rigid posterior strut 25 with the assistance of the stiff cuff members 55 and 57.

FIGS. 3 and 4 illustrate a functional brace 65 in accordance with the invention. The lower portion of brace 65 is shown open in FIG. 3 for application to the leg. In this brace, parts corresponding to similar parts in the prophylactic brace 23 of FIGS. 1 and 2 are identified by the same reference characters. This functional brace 65 also includes an inferior medial rigid elongated support member 67 pivotally connected to the terminal portion 33 of the rigid posterior strut 25 at a pivot point coaxial with the snap fastener 63. The functional brace 65 also includes a superior lateral support member 69 which is pivotally connected to the lateral terminal portion 31 of the strut 25 at a pivot point coaxial with the snap fastener 63, and is secured to the thigh by the straps 49.

The functional brace 65 also includes, in addition to the generally triangularly shaped anterior cuff members 55 and 57, posterior, semicylindrical stiff cuff members 71 and 73 which extend between the respective medial and lateral support members extending along the sides of the leg 13 and thigh 7, respectively.

The brace 65 includes additional stiff, semirigid anterior, generally triangular, cuff member 56, secured to elongated member 67 and connected by a snap fastener 63 to terminal portion 31, and cuff member 58, secured to elongated member 69 and connected by snap fastener 63 to terminal portion 33. These additional cuffs 56 and 58 criss-cross with the cuffs 55 and 57 anterior to the leg and thigh, respectively.

The functional brace 65 with both medial and lateral support members for the thigh and leg and the added cuff members, add additional support and stability to the knee joint.

Figure 5:
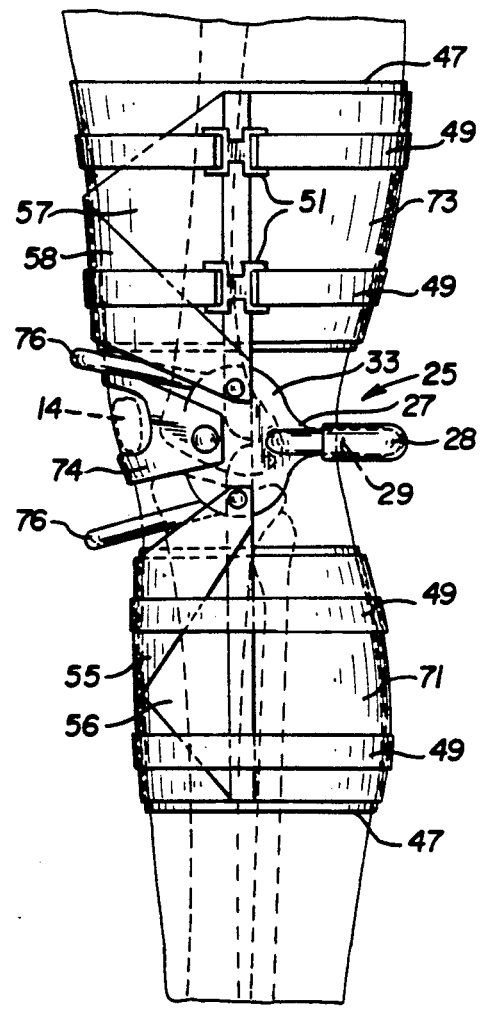
FIG. 5 is side elevation view of a knee brace in accordance with the invention with the leg in extension.
Figure 6:
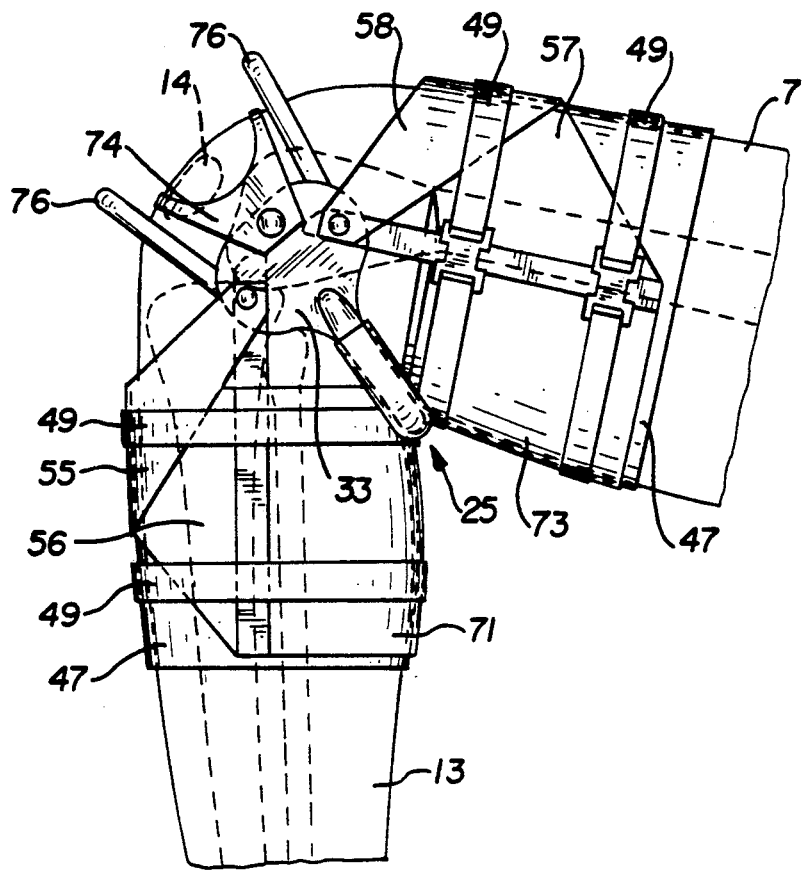
FIG. 6 is a side elevation view similar to FIG. 5 showing the leg in flexion.

Operation of knee braces in accordance with the invention is illustrated by FIGS. 5 and 6. With the leg extended as shown in FIG. 5, the rigid posterior strut 25 extends substantially horizontally, rearward into the popliteal area 29 behind the knee joint 1. When the joint is flexed as shown in FIG. 6, the fleshy posterior portions of the leg (the calf) and thigh reposition the rigid posterior strut 25. This repositioning rotates the terminal portions 31 and 33 so that the pivot points at which the inferior and superior support members are attached are rotated to accommodate for the femoral rollback which is illustrated in FIG. 6. Thus, in the knee braces in accordance with the invention, the brace is automatically positioned by the natural movement of the leg, thus eliminating the need for complex joint mechanisms which are sometimes ineffective because of slippage of the brace during flexion and extension.

FIGS. 5 and 6 also illustrates that one or two anterior struts 76 can be secured to the terminal portions 31 and 33 for protecting the knee joint 1 from forces acting frontally or posterior forces forcing the tibia forward. The forces generated by such action are transmitted through the strut 25 to the elongated support members for dissipation in the major muscles in the leg and thigh. The anterior struts 76 form with the posterior strut 25 a rigid support completely surrounding the knee joint and through which forces applied to the limb are transmitted around the knee joint.

The terminal portions 31 and 33 of the rigid posterior strut 25 also serve as reference or attachment points for other devices, such as for instance, a patella stabilizer 74 as shown in FIGS. 5 and 6.

Figure 7:
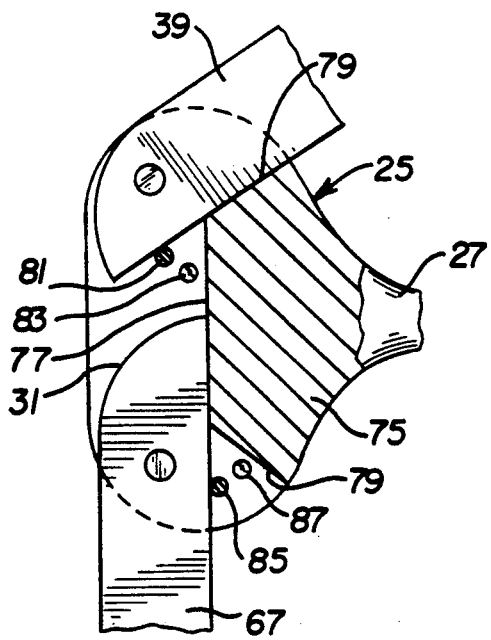
FIG. 7 is a vertical section through a terminal portion of the rear strut which forms a part of the knee brace of the invention.
Figure 8:
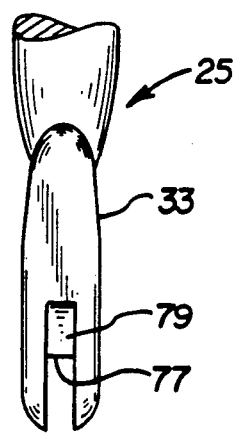
FIG. 8 is a top plan view of a terminal portion of the rear strut.

The hinges formed by the terminal portions 31 and 33 of the rigid posterior strut 25 and the elongated support members can be configured to limit movement of the joint for functional or rehabilitative applications. For instance, as shown in FIG. 7, which is a vertical section through the terminal portion 33 of the strut 25, a cam 75 has a vertical edge 77 which is engaged by the pivoting elongated support means such as 39 and 67 to limit extension of the joint, and biased shoulders 79 which restrict rotation of the elongated members to limit flexion of the joint. A pin 81 may be inserted in one of a number of holes 83 to limit extension of the knee joint to less than full extension. Similarly, a pin 85 may be inserted in a selected hole 87 to restrict flexion.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A brace for a knee joint joining thigh and leg limb members, said brace comprising:
   first and second rigid support members only;
   first anchoring means securing said first rigid support member to the thigh along a fleshy portion of a first side of the thigh with a lower end of said first rigid support member adjacent to but spaced from a first side of the knee joint;

second anchoring means securing said second rigid support member to the leg along a fleshy portion of a second side of the leg with an upper end of said second rigid support member adjacent to but spaced from a second side of the knee joint; and a rigid posterior strut having a first terminal portion pivotally connected at a first pivot point to said lower end of said first rigid support member and inwardly spaced from the first side of the knee joint, a second terminal portion pivotally connected at a second pivot point to said upper end of said second rigid support member and outwardly spaced from the second side of the knee joint, and a rigid arcuate section extending between said terminal portions through a popliteal space behind the knee joint, said rigid posterior strut being clamped between the thigh and leg to position said first and second pivot points upon flexion of the knee joint.

2. The brace of claim 1 including:

a first stiff anterior cuff member secured to said first rigid support member and extending around in front of the thigh and pivotally connected to said second terminal portion of said rigid posterior strut; and a second stiff anterior cuff member secured to said second rigid support member and extending around in front the leg and pivotally connected to said first terminal portion of said rigid posterior strut.

3. The knee brace of claim 2 wherein said first and second anchoring means each comprise sleeves which wrap around the thigh and respectively, 4. The knee brace of claim 3 wherein said first and second anchoring means further comprise strap means which wrap around said sleeve and engage and secure said rigid support members to the thigh and calf.

5. The knee brace of claim 2 wherein said first and second stiff anterior cuff members are each generally triangular members having a side edge and a vertex opposite the side edge, the side edge of said first stiff cuff member being secured along said first rigid support member and the vertex of the first stiff cuff member pivotally connected to said second terminal portion of said rigid posterior strut at a connection point laterally aligned with the first pivot point on said first terminal portion of said rigid posterior strut and the side edge of said second stiff cuff member being secured along said second rigid support member and the vertex of the second stiff cuff member pivotally connected to said first terminal portion of said rigid posterior strut at a connection point laterally aligned with said second pivot point on the second terminal portion of said rigid posterior strut.

6. The knee brace of claim 1 wherein said thigh, leg and knee joint have a medial side and a lateral side and wherein the first side is the medial side and the second side is the lateral side.

7. The knee brace of claim 5 wherein said thigh, leg and knee joint have a medial side and a lateral side and wherein the first side is the medial side and the second side is the lateral side.

8. The knee brace of claim 2 including limiting means limiting pivoting of said rigid support members relative to said first and second end portions of said rigid strut.

9. The knee brace of claim 5 including releasable pivoting connection means pivotally connecting the vertices of said first and second generally triangular anterior cuff members to said connection points.

10. A brace for a knee joint joining thigh and leg limb members, said brace comprising:

first, second, third and fourth rigid support members;

first anchoring means securing said first rigid support member to the thigh along a fleshy portion of a medial side of the thigh with a lower end of said first rigid support member adjacent to but spaced from a medial side of the knee joint, and securing said third rigid support member to said thigh along a fleshy portion of a lateral side of the thigh with a lower end of said third rigid support member adjacent to but spaced from a lateral side of the knee joint;

second anchoring means securing said second rigid support member to the leg along a fleshy portion of a lateral side of the leg with an upper end of said second rigid support member adjacent to but spaced from a lateral side of the knee joint, and securing said fourth rigid support member to the leg along a fleshy portion of a medial side of the leg with an upper end of said fourth rigid support member adjacent to but spaced from a lateral side of the knee joint;

a rigid posterior strut having a first terminal portion pivotally connected at a first pivot point to said lower end of said first rigid support member and pivotally connected at a fourth pivot point to said upper end of said fourth rigid support member and inwardly spaced from the medial side of said knee joint, a second terminal portion pivotally connected at a second pivot point to said upper end of said second rigid support member and pivotally connected at a third pivot point to the lower end of said third rigid support member and outwardly spaced from the lateral side of said knee joint, and a rigid arcuate section extending between said terminal portions through a popliteal space behind said knee joint, said rigid posterior strut being clamped between said thigh and leg to reposition said pivot points upon flexion of the knee joint to accommodate for femoral rollback; and first, second, third and fourth stiff anterior cuff members each generally triangular and having a side edge and a vertex opposite the side edge, the side edge of said first stiff cuff member being secured along said first rigid support member and the vertex of the first stiff cuff member pivotally connected to said second terminal portion of said rigid posterior strut at a connection point laterally aligned with the first pivot point on said first terminal portion of said rigid posterior strut, the side edge of said second stiff cuff member being secured along said second rigid support member and the vertex of the second stiff cuff member pivotally connected to said first terminal portion of said rigid posterior strut at a connection point laterally aligned with said second pivot point on the second terminal portion of said rigid posterior strut, the side edge of said third stiff cuff member being secured to said third rigid support member and the vertex of the third stiff cuff member pivotally connected to said first terminal portion of said rigid posterior strut at a connection point laterally aligned with the third pivot point on said second terminal portion of said rigid posterior strut, said third anterior cuff member extending around in front of the thigh and criss-crossing with said first stiff anterior cuff member, and the side edge of said fourth stiff cuff member being secured to said fourth rigid support member and the vertex pivotally connected to said second terminal portion of said rigid posterior strut at a connection point laterally aligned with said fourth pivot point on said second terminal portion of said rigid posterior strut, said fourth anterior cuff member extending around in front of the leg and criss-crossing with said second stiff anterior cuff member.

11. The knee brace of claim 10 including a first stiff, posterior cuff member extending between said first and third rigid support members posterior to the thigh and a second stiff posterior cuff member extending between said second and fourth rigid support members posterior to the calf.

12. The brace of claim 10 including releasable pivoting connection means pivotally connecting the vertices of said generally triangular anterior cuff members at said connection points.

13. The knee brace of claim 8 wherein said limiting means comprise cam means on said terminal portion of said rigid posterior strut, said cam means having first shoulder means placed to limit rotation of said rigid members during extension and second shoulder means placed to limit opposite rotation of said rigid support members during flexion.

14. The knee brace of claim 8 wherein said limiting means comprises pins insertable in a selected hole in said terminal portions of said rigid posterior strut to selectively limit flexion and extension.

* * * * *